(12) United States Patent
Wisdom et al.

(10) Patent No.: US 6,423,522 B1
(45) Date of Patent: Jul. 23, 2002

(54) MICROORGANISM LACTAMASE ENZYME OBTAINED THEREFROM AND THEIR USE

(75) Inventors: Richard Anthony Wisdom, Cambridge; Caroline Susan Lee, Cambridgeshire; Robert Christopher Brown, Cambridge, all of (GB)

(73) Assignee: Chirotech Technology, Ltd. (GB)

( * ) Notice: Subject to any disclaimer, the term of this patent is extended or adjusted under 35 U.S.C. 154(b) by 0 days.

(21) Appl. No.: 09/510,949

(22) Filed: Feb. 22, 2000

Related U.S. Application Data

(62) Division of application No. 08/922,865, filed on Sep. 3, 1997, now Pat. No. 6,090,616.

(30) Foreign Application Priority Data

Sep. 3, 1996 (GB) .............................................. 9618340

(51) Int. Cl.⁷ .................................................. C12N 9/14
(52) U.S. Cl. ....................... 435/195; 435/174; 435/176; 435/177; 435/231; 435/227
(58) Field of Search ................................. 435/174, 176, 435/177, 195, 231, 227

(56) References Cited

FOREIGN PATENT DOCUMENTS

EP          0424064          4/1991

OTHER PUBLICATIONS

Taylor, S.J.C., R. McCague, R. Wisdom, C. Lee, K. Dickson, G. Ruecroft, F. O'Brien, J. Littlechild, J. Beven, S. Roberts, C. Evans (1993) "Development of the Biocatalytic Resolution of 2–azabicyclo[2.2.1]hept–5–en–3–one as an entry to Single–Enantiomer Carbocyclic Nucleosides" *Tetrahedron Asymmetry* 4(6):1117–1128.

Brabban, A.D., J. Littlechild, R. Wisdom (1996) Stereospecific γ–lactamase activity in a *Pseudomonas fluorescens* species *Journal of Industrial Microbiology* 16:8–14.

Krieg, N.R. (1984) "Bergey's manual of systematic bacteriology" see p. 78, right–hand column and pp. 179–180, abstract No. XP002048230.

*Primary Examiner*—Francisco Prats
(74) *Attorney, Agent, or Firm*—Saliwanchik, Lloyd & Saliwanchik

(57) ABSTRACT

A lactamase enzyme having good stability, capable of hydrolysing an enantiomer of the bicyclic lactam, 2-azabicyclo[2.2.1]hept-5-en-3-one, to give (−) lactam and (+) amino acid, has been found in a strain of *Comamonas acidivorans*. The enzyme has been isolated and cloned, and its structure identified.

8 Claims, No Drawings

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 1951 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Comamonas acidovorans (ix) FEATURE:
      (A) NAME/KEY: CDS
      (B) LOCATION:49..1773

(xi) SEQUENCE DESCRIPTION: SEQ ID NO: 1:

```
CGCTCGTATG TTGGGATGTG AGCGATACAA TTTCACACAG GAACAGCT ATG ACC ATG       57
                                                    Met Thr Met
                                                      1

ATA ACG CCA AGC TTG CAT GCC TCG GCA GGT CGG ACT CTA GAG GAT CCG      105
Ile Thr Pro Ser Leu His Ala Ser Ala Gly Arg Thr Leu Glu Asp Pro
        5                  10                  15

TTT TTT CCC ACT GCC ATC GCA AGG AGC ACA CCA TGG CCG GAA ACC CTG      153
Phe Phe Pro Thr Ala Ile Ala Arg Ser Thr Pro Trp Pro Glu Thr Leu
 20                  25                  30                  35

ATC AAG GTC GAT CTC AAC CAG TCC CCC TAC GAC AAC CCG CAG GTG CAC      201
Ile Lys Val Asp Leu Asn Gln Ser Pro Tyr Asp Asn Pro Gln Val His
                40                  45                  50

AAC CGC TGG CAT CCC GAC ATT CCC ATG GCG GTC TGG GTG GAG CCG GGC      249
Asn Arg Trp His Pro Asp Ile Pro Met Ala Val Trp Val Glu Pro Gly
            55                  60                  65

GCG GAG TTC AAG CTG GAG ACC TAT GAC TGG ACC GGC GGC GCC ATC AAG      297
Ala Glu Phe Lys Leu Glu Thr Tyr Asp Trp Thr Gly Gly Ala Ile Lys
        70                  75                  80

AAC GAC GAC AGC GCC GAA GAC GTG CGC GAC GTG GAT CTG TCC ACC GTC      345
Asn Asp Asp Ser Ala Glu Asp Val Arg Asp Val Asp Leu Ser Thr Val
 85                  90                  95

CAC TTC CTG TCC GGC CCC GTG GGC GTG AAG GGC GCG CAG CCC GGC GAC      393
His Phe Leu Ser Gly Pro Val Gly Val Lys Gly Ala Gln Pro Gly Asp
100                 105                 110                 115

CTG CTG GTG GTG GAC CTG CTG GAC ATC GGC GCG CGC GAC GAC AGC CTC      441
Leu Leu Val Val Asp Leu Leu Asp Ile Gly Ala Arg Asp Asp Ser Leu
                120                 125                 130

TGG GGC TTC AAC GGC TTT TTC TCC AAG CAG AAT GGC GGC GGC TTC CTG      489
Trp Gly Phe Asn Gly Phe Phe Ser Lys Gln Asn Gly Gly Gly Phe Leu
            135                 140                 145

GAC GAG CAT TTC CCG CTG GCC CAG AAG TCC ATC TGG GAC TTC CAC GGC      537
Asp Glu His Phe Pro Leu Ala Gln Lys Ser Ile Trp Asp Phe His Gly
        150                 155                 160

ATG TTC ACC AAG AGC CGC CAC ATC CCC GGC GTC AAC TTC GCA GGC CTC      585
Met Phe Thr Lys Ser Arg His Ile Pro Gly Val Asn Phe Ala Gly Leu
165                 170                 175
```

-continued

```
ATC CAC CCG GGC CTG ATC GGC TGC CTG CCC GAC CCC AAG ATG CTG GCC        633
Ile His Pro Gly Leu Ile Gly Cys Leu Pro Asp Pro Lys Met Leu Ala
180             185                 190                 195

AGC TGG AAT GAG CGC GAG ACC GGC CTC ATC GCC ACC GAC CCC GAC CGC        681
Ser Trp Asn Glu Arg Glu Thr Gly Leu Ile Ala Thr Asp Pro Asp Arg
                200                 205                 210

ATT CCC GGC CTG GCC AAC CCG CCC AAC GCC ACC ACC GCC CAC ATG GGC        729
Ile Pro Gly Leu Ala Asn Pro Pro Asn Ala Thr Thr Ala His Met Gly
            215                 220                 225

CAG ATG CAG GGC GAG GCG CGC GAC AAG GCC GCC GCC GAA GGC GCA CGC        777
Gln Met Gln Gly Glu Ala Arg Asp Lys Ala Ala Ala Glu Gly Ala Arg
        230                 235                 240

ACC GTG CCG CCG CGC GAG CAC GGC GGC AAC TGC GAC ATC AAG GAC CTC        825
Thr Val Pro Pro Arg Glu His Gly Gly Asn Cys Asp Ile Lys Asp Leu
    245                 250                 255

TCG CGC GGC TCG CGC GTG TTC TTC CCC GTC TAC GTG GAC GGC GCG GGC        873
Ser Arg Gly Ser Arg Val Phe Phe Pro Val Tyr Val Asp Gly Ala Gly
260                 265                 270                 275

CTG AGC GTG GGC GAC CTG CAC TTC AGC CAG GGT GAT GGC GAG ATC ACC        921
Leu Ser Val Gly Asp Leu His Phe Ser Gln Gly Asp Gly Glu Ile Thr
                280                 285                 290

TTC TGG GGG CCC ATC GAG ATG CCC GGC TGG GTG CAC ATG AAG GTC TCG        969
Phe Trp Gly Pro Ile Glu Met Pro Gly Trp Val His Met Lys Val Ser
            295                 300                 305

CTG ATC AAG GGC GGC ATG GCC AAG TAC GGC ATC AAG AAC CCC ATC TTC       1017
Leu Ile Lys Gly Gly Met Ala Lys Tyr Gly Ile Lys Asn Pro Ile Phe
        310                 315                 320

AAG CCC AGC CCC ATG ACG CCC AAC TAC CAA GGA CTA CCT GAT CTT CGA       1065
Lys Pro Ser Pro Met Thr Pro Asn Tyr Gln Gly Leu Pro Asp Leu Arg
    325                 330                 335

AGG CAT CTC GGT GGA CGA AAA GGG CAA GCA GCA CTA CCT GGA CGT GAC       1113
Arg His Leu Gly Gly Arg Lys Gly Gln Ala Ala Leu Pro Gly Arg Asp
340                 345                 350                 355

CGT GGC CTA CCG CCA GGC CTG CCT GAA CGC CAT CGA GTA CCT GAA GAA       1161
Arg Gly Leu Pro Pro Gly Leu Pro Glu Arg His Arg Val Pro Glu Glu
                360                 365                 370

ATT CGG CTA CAG CGG CGC CCA GGC CTA CTC GCT GCT GGG CAC GGC GCC       1209
Ile Arg Leu Gln Arg Arg Pro Gly Leu Leu Ala Ala Gly His Gly Ala
            375                 380                 385

CGT GCA GGG CCA CAT CAG CGG CGT GGT GGA CGT GCC CAA TGC CTG CGC       1257
Arg Ala Gly Pro His Gln Arg Arg Gly Gly Arg Ala Gln Cys Leu Arg
        390                 395                 400

CAC GCT GTG GCT GCC CAC GGA GAT CTT CGA CTT CGA CAT CAA TCC CAC       1305
His Ala Val Ala Ala His Gly Asp Leu Arg Leu Arg His Gln Ser His
    405                 410                 415

GGC CGA GGG ACC ACA GAA GAT CAT CAC GGG CGG GGT GGA TCT GCC CAT       1353
Gly Arg Gly Thr Thr Glu Asp His His Gly Arg Gly Gly Ser Ala His
420                 425                 430                 435

CGC CCA GGA CAA GTA AGC CCG GCA TAC GAC ACC CGC CAT CCA CCA TTC       1401
Arg Pro Gly Gln Val Ser Pro Ala Tyr Asp Thr Arg His Pro Pro Phe
                440                 445                 450

GCC AGA GGC CGC CCA TGC CCA CCT ATG ACT ACC ACT GCA CCG CAT GCG       1449
Ala Arg Gly Arg Pro Cys Pro Pro Met Thr Thr Thr Ala Pro His Ala
            455                 460                 465

GCG GCT TCG ACG CGC TGC GCA GCC TCT CGC AGC GCA ACG AGC CCG CGC       1497
Ala Ala Ser Thr Arg Cys Ala Ala Ser Arg Ser Ala Thr Ser Pro Arg
        470                 475                 480

CCT GCC CCA GCT GCG AGG CGG CCT CGC CCC GCG TCT TCG TCA GCG CGC       1545
Pro Ala Pro Ala Ala Arg Arg Pro Arg Pro Ala Ser Ser Ser Ala Arg
    485                 490                 495
```

-continued

```
CGC GCC TGG CCT GCA CCA GCC CCG AAC AGC GCC GCG CCC ACG ACA CCA      1593
Arg Ala Trp Pro Ala Pro Ala Pro Asn Ser Ala Ala Pro Thr Thr Pro
500                 505                 510                 515

ACG AGC GCG CCC GGC ACG AGC CCA GGC GCT CAC GCG ATG TGG CCG AGG      1641
Thr Ser Ala Pro Gly Thr Ser Pro Gly Ala His Ala Met Trp Pro Arg
                520                 525                 530

GCA GCT ACG CGC GCA TGC GCC ACC CCA TCG GGC TGC GGC TGC TGC AGC      1689
Ala Ala Thr Arg Ala Cys Ala Thr Pro Ser Gly Cys Gly Cys Cys Ser
            535                 540                 545

GGC GCC AGC AAG CGC GGC TCC ACG GTC ACG GCG CCC AAC GGC GCC AAG      1737
Gly Ala Ser Lys Arg Gly Ser Thr Val Thr Ala Pro Asn Gly Ala Lys
        550                 555                 560

ACC TTC CCG ACC AAG CGG CCC TGG ATG ATC AGC CAC TGACCGCGGA           1783
Thr Phe Pro Thr Lys Arg Pro Trp Met Ile Ser His
    565                 570                 575

CCCTGCGCCG CACCAATGAC AAGGGCCCGC GACGCGGGCC TTTGTCCTGC CTGGCCGTAC    1843

CGCTCAGTGC ACGGCGCCGA TGAAGCCGGC CAGCTCCGGC GTCTGCGGGT TGGCGAACAG    1903

CTGCTTGGCC CGGGGCCGCT TTCGTGGATC CCCGGTACCG AATCGATC                 1951
```

(2) INFORMATION FOR SEQ ID NO: 2:

(i) SEQUENCE CHARACTERISTICS:
        (A) LENGTH: 575 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Thr Met Ile Thr Pro Ser Leu His Ala Ser Ala Gly Arg Thr Leu
 1               5                  10                  15

Glu Asp Pro Phe Phe Pro Thr Ala Ile Ala Arg Ser Thr Pro Trp Pro
                20                  25                  30

Glu Thr Leu Ile Lys Val Asp Leu Asn Gln Ser Pro Tyr Asp Asn Pro
            35                  40                  45

Gln Val His Asn Arg Trp His Pro Asp Ile Pro Met Ala Val Trp Val
        50                  55                  60

Glu Pro Gly Ala Glu Phe Lys Leu Glu Thr Tyr Asp Trp Thr Gly Gly
65                  70                  75                  80

Ala Ile Lys Asn Asp Asp Ser Ala Glu Asp Val Arg Asp Val Asp Leu
                85                  90                  95

Ser Thr Val His Phe Leu Ser Gly Pro Val Gly Val Lys Gly Ala Gln
                100                 105                 110

Pro Gly Asp Leu Leu Val Val Asp Leu Leu Asp Ile Gly Ala Arg Asp
            115                 120                 125

Asp Ser Leu Trp Gly Phe Asn Gly Phe Phe Ser Lys Gln Asn Gly Gly
        130                 135                 140

Gly Phe Leu Asp Glu His Phe Pro Leu Ala Gln Lys Ser Ile Trp Asp
145                 150                 155                 160

Phe His Gly Met Phe Thr Lys Ser Arg His Ile Pro Gly Val Asn Phe
                165                 170                 175

Ala Gly Leu Ile His Pro Gly Leu Ile Gly Cys Leu Pro Asp Pro Lys
                180                 185                 190

Met Leu Ala Ser Trp Asn Glu Arg Glu Thr Gly Leu Ile Ala Thr Asp
            195                 200                 205

Pro Asp Arg Ile Pro Gly Leu Ala Asn Pro Pro Asn Ala Thr Thr Ala
```

```
                    210                 215                 220
His Met Gly Gln Met Gln Gly Glu Ala Arg Asp Lys Ala Ala Ala Glu
225                 230                 235                 240

Gly Ala Arg Thr Val Pro Pro Arg Glu His Gly Gly Asn Cys Asp Ile
                    245                 250                 255

Lys Asp Leu Ser Arg Gly Ser Arg Val Phe Phe Pro Val Tyr Val Asp
                    260                 265                 270

Gly Ala Gly Leu Ser Val Gly Asp Leu His Phe Ser Gln Gly Asp Gly
                275                 280                 285

Glu Ile Thr Phe Trp Gly Pro Ile Glu Met Pro Gly Trp Val His Met
    290                 295                 300

Lys Val Ser Leu Ile Lys Gly Gly Met Ala Lys Tyr Gly Ile Lys Asn
305                 310                 315                 320

Pro Ile Phe Lys Pro Ser Pro Met Thr Pro Asn Tyr Gln Gly Leu Pro
                    325                 330                 335

Asp Leu Arg Arg His Leu Gly Gly Arg Lys Gly Gln Ala Ala Leu Pro
                340                 345                 350

Gly Arg Asp Arg Gly Leu Pro Pro Gly Leu Pro Glu Arg His Arg Val
            355                 360                 365

Pro Glu Glu Ile Arg Leu Gln Arg Arg Pro Gly Leu Leu Ala Ala Gly
    370                 375                 380

His Gly Ala Arg Ala Gly Pro His Gln Arg Arg Gly Gly Arg Ala Gln
385                 390                 395                 400

Cys Leu Arg His Ala Val Ala Ala His Gly Asp Leu Arg Leu Arg His
                405                 410                 415

Gln Ser His Gly Arg Gly Thr Thr Glu Asp His His Gly Arg Gly Gly
                420                 425                 430

Ser Ala His Arg Pro Gly Gln Val Ser Pro Ala Tyr Asp Thr Arg His
                435                 440                 445

Pro Pro Phe Ala Arg Gly Arg Pro Cys Pro Pro Met Thr Thr Thr Ala
    450                 455                 460

Pro His Ala Ala Ala Ser Thr Arg Cys Ala Ala Ser Arg Ser Ala Thr
465                 470                 475                 480

Ser Pro Arg Pro Ala Pro Ala Ala Arg Arg Pro Arg Pro Ala Ser Ser
                485                 490                 495

Ser Ala Arg Arg Ala Trp Pro Ala Pro Ala Pro Asn Ser Ala Ala Pro
            500                 505                 510

Thr Thr Pro Thr Ser Ala Pro Gly Thr Ser Pro Gly Ala His Ala Met
        515                 520                 525

Trp Pro Arg Ala Ala Thr Arg Ala Cys Ala Thr Pro Ser Gly Cys Gly
    530                 535                 540

Cys Cys Ser Gly Ala Ser Lys Arg Gly Ser Thr Val Thr Ala Pro Asn
545                 550                 555                 560

Gly Ala Lys Thr Phe Pro Thr Lys Arg Pro Trp Met Ile Ser His
                565                 570                 575
```

MICROORGANISM LACTAMASE ENZYME OBTAINED THEREFROM AND THEIR USE

CROSS-REFERNCE TO RELATED APPLICATION

This application is a division of application Ser. No. 08/922,865, filed Sep. 3,1997 now U.S. Pat. No. 6,090,616.

FIELD OF THE INVENTION

This invention relates to a microorganisms lactamase enzyme obtained therefrom, and their use.

BACKGROUND OF THE INVENTION

The bicyclic γ-lactam, 2-azabicyclo 2.2.1hept-5-en-3-one, is a useful synthon hat can be used for the production of carbocyclic nucleosides which are gaining in importance as therapeutic agents. Published areas to which such nucleosides are being targeted include antivirals (e.g. Vince and Hua. J. Med. Chain., 33:17–21 (1990), againts e.g. HIV) and cardiac vasodilators (adenosine agonists). A major benefit of the carbocyclyc in such agents is its resistance to breakdown by enzymes in the body. By comparison, naturally-occurring ribosyl nucleosides may be more readily cleaved by nucleases, so that their bioactivity is lost.

Although carbocyclic nucleosides are known in nature e.g. Aristeromycin from *Streptomyces citricolor*, natural yields tend to be low and the isolated products have then to be further manipulated to obtain more useful compounds. A more econonic route is to synthesise the required compounds chemically, sarting from the γ-lactam. However, as chemically synthesised, γ-lactam is racemic By conventional synthesis, the ultimate drug will also be a mixture of enantiomers, which causes regulatory concerns if one of the enantiomers is not very active or causes unwanted side-efects. There is a need therefore to put a step into the synthesis where either of the two enantiomers of a racemic synthon can be isolated and the rest of the drug then built on it.

An effective way of doing this is to use an enzyme to selectively hydrolyse one enantiomer of the racemic γ-lactam across the amide bond, to give the cyclic amino acid compound and leave the other enantiomer. The remaining lactam can then be readily separated from the amino acid product by extraction into dichloromethane, purfied by crystailltisation and used in subsequent downstream chemistry to build up the required drug. By careful selection of the right enzyme it is possible to find an enzyme highly selectively for only one of the lactam enantiomers such that at marginally greater than 50% conversion, lactam of high ee (>90%) remains. Enzymes have been found that are selective for either of the two enantiomers.

EP-A-0424064 discloses methods for carrying out the above described resolution and provides two organisms that produce enzymes that have the different selectivities. A Rhodococcus strain produces an enzyme which hydrolyses the (−) lactam, enabling the (+) lactam to be isolated for further use. whereas a Pseudomonad produces an emzyme which hydrolyses the (+) lactam, enabling isolation of the (−) lactam.

Further enzymes that carry out these selective hydrolyses have also been described in the literature. Thus Taylor et al, Tetrahedron: Asymmetry, 4 (6):1117–1128 (1993), describe an enzyme selective for hydrolysis of the (+) lactam from a strain of *Pseudonomas fluorescens* and an enzyme selective for the (−) lactam from a strain of Aureobacterium. A further enzyme selective for the hydrolysis of the (+) lactam has been described by Brabban et al. J. Ind. Microbiology. 16:8–14 (1996).

In order to develop a robust industrial biotransformation process, it is desirable to use an enzyme or whole cell biocatalyst that is relatively stable. This can enable biocatalyst recycling and re-use through immobilisation, thus greatly reducing biocatalyst cost and enabling handling of the biocatalyst on a large scale without significant losses of activity. It is also often found that more stable biocatalysts are better able to tolerate high substrate and/or product concentrations without inactivation. This then enables biotransformation to be run at the highest concentration of reactants possible, given kinetic and handling constraints. This has two advantages: it results in minimal reactor volume requirements and also minimises liquid handing volumes during product work-up.

Taylor et al, supra. describe a lactamase from Aireobacterium especies that is very stable at elevated temperatures and which selectively hydrolyses the (−) γ-lactam, giving the (+) γ-lactam and (−) amino acid as a product. The enzyme from this organism has been immobilised and maintains its stability over months of operation. No enzyme with good stability and the opposite selectivity is known, although Brabban at al, Supra, screened a number of different potential isolates. Previous work with Pseudomonad type organisms displaying the required lactamase activity had shown them to have poor stability. This is unfortunate since it is the (−) γ-lactam which is the more usefwl synthon, having the more natural stereochemistry and making it easier to build up functionality than for instance the (−) amino acid formed by the action of the Aireobacterium lactamase. There is therefore a need for a stable γ-lactamase with high selectivity for the hydrolysis of the (+) bicyclic γ-lactam.

SUMMARY OF THE INVENTION

Surprisingly, it has been found that a strain of *Comamonas acidivorans*, which was isolated from the environment, produces an enzyme of high potential for use in an industrial process for resolution of the required γ-lactam. This enzyme is not only much more temperature-stable than previously identified (+) γ-lactamase, but it also enables the bioresolution to be carried out at very high substrate/product concentrations. This organism has been deposited at the NCIMB, 23 St. Machar Street, Aberdeen, UK, on 30th August 1996, under the terms of the Budapest Treaty, where it has been given the accession number NCIMB 40827.

The gene encoding the γ-lactamase has been isolated and sequenced (see SEQ ID NO:1), and the enzyme's amino-acid sequence derived (see SEQ ID NO:2). This invention relates to compounds having this structure, and fragments thereof having the same activity, as will be readily evident to one of ordinary skill in the art. The novel enzyme is characterised by its stability, i.e. one or more of the following:

greater than 85% retention of activity after being held at 40° C. for 4 hours or greater than 30% activity after being held at 60° C. for 4 hours;

hydrolysis at an initial concentration of 100 g racemic lactam plus 300 ml buffer and continuing to at least 90% hydrolysis of the (+) lactam with less than 5% hydrolysis of the (−) lactam.

DESCRIPTION OF THE INVENTION

The novel enzyme is useful for the enantiospecific hydrolysis of a mixture of enantiomers of the required γ-lactam, e.g. a racemic mixture. After reaction, the residual (−) lactam may readily be separated from the (+) amino-acid formed by hydrolysis. Both these reactions may be conducted under conditions known to those of ordinary skill in the art.

The enzyme may be used in whole cell or isolated form. It may be immobilised, if desired, by methods known to those of ordinary skill in the art.

The enzyme may be produced from the deposited organism. Alternatively, it may be produced by recombinant technology.

Using the DNA and amino-acid sequence provided herein, a person skilled in the art can readily construct fragments or mutations of the genes and enzymes disclosed herein. These fragments and mutations, which retain the activity of the exemplified enzyme, are within the scope of the present invention. Also, because of the redundancy of the genetic code, a variety of different DNA sequences can encode the amino-acid sequences disclosed herein. It is well within the skill of one of ordinary skill in the art to create these alternative DNA sequences encoding the same, or similar, enzymes. These DNA sequences are within the scope of the present invention. As used herein, reference to "essentially the same" sequence refers to sequences which have amino-acid substitutions, deletions, additions or insertions which do not materially affect activity. Fragments retaining activity are also included in this definition.

The genes of this invention can be isolated by known procedures and can be introduced into a wide variety of microbial hosts. Expression of the gene results, directly or indirectly, in the intracellular production and maintenance of the enzyme. The gene may be introduced via a suitable vector into a microbial host.

A wide variety of ways are available for introducing the gene into the microorganism host under conditions which allow for stable maintenance and expression of the gene. A DNA construct may include the transcriptional and translational regulatory signals for expression of the gene, the gene under their regulatory control and a DNA sequence homologous with a sequence in the host organism, whereby integration will occur, and/or a replication system which is functional in the host, whereby integration or stable maintenance will occur.

In the direction of transcription, namely in the 5' to 3' direction of the coding or sense sequence, the construct can involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker.

The gene can be introduced between the transcriptional/translational initiation and termination regions, so as to be under the regulatory control of the initiation region. This construct can be included in a plasmid, which could include at least one replication system, but may include more than one, where one replication system is employed for cloning during the development of the plasmid and the second replication system is necessary for functioning in the ultimate host. In addition, one or more markers may be present, as described above. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for activity.

Suitable host cells include prokaryotes and eukarotes. An example is *E. coli*.

The following Examples illustrate the invention.

1. Isolation of Potential γ-Lactamase Producing Straints

Approximately 1 g of soil from a ditch was mixed with 20 ml 50 mM potassium phosphate buffer, pH7, mixed well and shaken at room temperature for 30 minutes. A 0.4% inoculum of this suspension was then placed into 25 ml enrichment medium in a conical flask and shaken at 30° C. for 41 hours. The following enrichment medium was used:

|  | $(g \cdot l^{-1})$ |
| --- | --- |
| Yeast extract | 0.1 |
| $NH_4Cl$ | 2.0 |
| $KH_2PO_4$ | 7.0 |
| $Na_2HPO_4$ | 2.0 |
| $MgSO_4$ | 0.4 |
| $CaCl_2$ | 0.2 |
| Trace element solution | 0.2 |
| Racemic bicyclic γ-lactam | 2.0 |
| 5M NaOH | to pH 7 | the trace element solution comprised:

|  | $(g \cdot l^{-1})$ |
| --- | --- |
| $CaCl_2.2H_2O$ | 3.6 |
| ZnO | 2.0 |
| $CuCl.2H_2O$ | 0.85 |
| $Na_2MoO.2H_2O$ | 4.8 |
| $MnCl_2.4H_2O$ | 2.0 |
| $FeCl_3.6H_2O$ | 5.4 |
| $H_3BO_3$ | 0.3 |
| $CoCl_2.6H_2O$ | 2.4 |
| Conc HCl | 250 ml |

A 0.5% inoculum was then transfered into a second enrichment flask (25 ml) of the same medium, and grown for a further 94 hours. At this point, samples were taken from the flask, diluted in 10 mM phosphate buffer, pH 7.0 and plated onto the following medium:

|  | $(g \cdot l^{-1})$ |
| --- | --- |
| Yeast extract | 0.1 |
| $NH_4Cl$ | 2.0 |
| $KH_2PO_4$ | 7.0 |
| $Na_2HPO_4$ | 2.0 |
| $MgSO_4$ | 0.4 |
| $CaCl_2$ | 0.2 |
| Trace element solution | 0.2 |
| Noble Agar | 15.0 |
| 5M NaOH | to pH 7 |

2.0 g.l$^{-1}$ N-acetyl-L-phenylanaline was then filter sterilised into the above autoclave medium on cooling, prior to pouring the plates. After 6 days incubation at 30° C., colonies were picked, and purified on further agar plates and then used in the screening study.

2. Screening of Recovered Isolates

Isolated colonies were grown in the following medium:

|  | (g · l⁻¹) |
| --- | --- |
| Yeast extract | 5.0 |
| NH₄Cl | 2.0 |
| KH₂PO₄ | 7.0 |
| Na₂HPO₄ | 2.0 |
| MgSO₄ | 0.4 |
| CaCl₂ | 0.2 |
| Trace element solution | 1.0 |
| Racemic bicyclic γ-lactam | 2.0 |
| Glucose | 10.0 |
| 5M NaOH | to pH 7 |

A colony was inoculated into 4 ml filter-sterilised medium in a sterile plastic container and grown for about 24 hours in a shaker at 30° C.

Cultures were then centrifuged and the pellet resuspended in 1 ml 50 mM phosphate buffer, pH7. To this was then added 1 ml 100 g.l⁻¹ racemic bicyclic γ-lactam in a similar buffer. Reactions were carried out at 30° C. with shaking. Samples were taken over the next 7 days and assayed for conversion of the lactam by HPLC. For those reactions showing significant hydrolysis, enantiomeric excess (ee) was determined by GC.

One strain which was isolated showed desirable characteristics. In the initial screen this strain achieved 52% conversion of the added substrate after 144 hours biotransformation, and the residual lactam was shown to be the (−) enantiomer with an ee of >99%. Identification by the NCIMB showed the organism to be a strain of *Comamonas acidovorans*. This strain has been deposited at the NCIMB, as described above.

The following analytical methods were employed:

Extent of Hydrolysis (HPLC). Samples were diluted as appropriate and 20 μl injected onto a 15 cm Kromasil C-8 column. The elution buffer was 50% methanol in 10 mM phosphate buffer, pH 7;. flow rate 1 ml.min⁻¹; run time 5 minutes. Detection was at λ=225 nm.

ee of reaction products (GC). Samples were extracted into ethyl acetate, dried with anhydrous magnesium sulphate and injected onto a 50 m CP Cyclodextrin capillary column. The oven temperature was increased from an initial 140 to 200° C. during the analysis.

3. Fermentation

Seed flasks were prepared using the following medium:

|  | (g · l⁻¹) |
| --- | --- |
| Yeast extract | 10 |
| (NH₄)₂SO₄ | 1 |
| KH₂PO₄ | 5 |
| MgSO₄.7H₂O | 0.1 |
| CaCl₂.2H₂O | 0.05 |
| Trace elements | 0.1 |
| NaOH | to pH 7 |

The trace element solution is as defined above, except that the amount of conc. HCl is 333 ml.l⁻¹.

75 ml medium was prepared in a 500 ml conical flask. Flasks were inoculated with the organism, and incubated with shaking at 25° C. till an absorbance (520 nm) of between 3.5 and 7 had been achieved. Cells were then inoculated at 0.1% into the fermenter having 1.5 L of the following (sterilised) medium:

|  | (g · l⁻¹) |
| --- | --- |
| Yeast extract | 20 |
| (NH₄)₂SO₄ | 2 |
| KH₂PO₄ | 5 |
| MgSO₄.7H₂ | 0.5 |
| CaCl₂.2H₂O | 0.1 |
| Trace elements | 1.0 |
| Succinic acid | 10 |
| PPG 2025 | 2 ml |
| NaOH | to pH 7 |

Initial temperature was 25° C. and the pH was controlled at 7.1. A constant air flow rate of about 0.5 vvm was maintained, with the agitation being varied between 500 and 1000 rpm to maintain aerobic conditions. After 18.6 hours, a slow feed of concentrated yeast extract was initiated at a rate equivalent to 2 g yeast extract added per initial litre per hour, i.e. 3 g per hour. The fermentation was completed 24 hours later, the cells harvested by centrifugation and stored as a cell paste in the freezer for further use. A total biomass of about 82 g wet cells was collected and the final fermentation activity yield was 0.45 U.ml⁻¹ (where 1 U is 1 μmole γ-lactam hydrolysed per minute).

4. Temperature Stability 35.8 g of cell paste was thawed and added to 700 ml lysis buffer, containing 10 mM sodium phosphate (pH 7), 10 mM EDTA, 0.1% Triton X-100, 5 mM dithiothreitol and 1 mg.ml⁻¹ lysozyme. The lysis buffer was stirred at room temperature for 5.5 hours, then 37 ml of a 5% solution of polyethylenimine, adjusted to pH 7 with HCl, was added and stirred for a further hour before recovering the supernatant by centrifugation.

To 500 ml supernatant was slowly added 174 g ammonium sulphate with good mixing to dissolve the salt. After 20 minutes, the precipitate was harvested by centrifugation and resuspended with 100 ml 10 mM sodium phosphate, pH 7. This was then dialysed against 2 times 5 L 10 mM sodium phosphate, pH 7.1, and then stored in the freezer.

For the temperature stability tests, the frozen dialysate was thawed and 2×2.5 ml samples buffer exchanged into 3.5 ml phosphate-buffered saline (PBS) or 10 mM Tris buffer, pH 8.0 using mini Sephadex G-25 gel filtration columns. Buffer exchange into the 10 mM Tris buffer resulted in a precipitate (which contained some activity) which was removed by centrifugation. Samples of each preparation were then placed in a 60° C. hot block, a 40° C. water bath or a 25° C. incubator. Samples were taken at 1, 2 and 4.3 hours and analysed for residual lactamase activity. The following results were obtained after 4.3 hours incubation:

| Buffer | Temperature (° C.) | Residual Activity (% of start) |
| --- | --- | --- |
| PBS | 25 | 97 |
| PBS | 40 | 87 |
| PBS | 60 | 32 |
| Tris (pH 8) | 25 | 110 |
| Tris (pH 8) | 40 | 105 |
| Tris (pH 8) | 60 | 45 |

By comparison, the *Pseudomonas fluorescens* γ-lactamase described by Brabban et al, supra, lost up to 70–80% of its activity over 4 hours at 37° C. The novel enzyme is clearly much more temperature-stable. This opens up the possibility of immobilising the enzyme onto a solid support and re-using it in many biotransformations, thereby greatly reducing its cost impact on the process.

5. Whole-cell Biotransformation

Frozen cell paste (25 g), obtained in a similar fermentation to that described in Example 3, excepting that the final enzyme yield in this case was measured to 0.67 U.ml$^{-1}$, was thawed and stirred in 50 mM KH$_2$PO$_4$ (300 ml, pH7). γ-Lactam (100 g) was added as solid to this, then the reaction stirred at 25° C. for 24 hours. Celite (28 g) then polyethylenimine (28 ml of 5% solution in water) were added, followed by isopropanol (175 ml). After stirring for a further 10 minutes, the solids were removed by filtration, then the filtrate evaporated in vacuo to 200 ml volume. The aqueous was extracted 5 times with dichloromethane (200 ml), then the organic extracts dried using anhydrous MgSO$_4$. The filter-cake was washed with acetone (150 ml) and the extract dried (with anhydrous MgSO$_4$), then all the combined organic fractions evaporated in vacuo to dryness. This yielded 44.3 g of an off-white solid, which was analysed to be (−) lactam having an ee of >99%.

This biotransformation could be carried out at a very high substrate concentration (1 g substrate per 3 ml buffer) and could still provide complete hydrolysis of the (+) lactam enantiomer. This is therefore highly volume-efficient, which enables the (−) lactam to be produced in a minimal volume, thus reducing liquid handling requirements and reducing batch biotransformation reactor volume requirements.

6. Identification and Isolation of the Gene

A quantity of cell paste (500 mg) was treated by the addition of TESS buffer (50 mM Tris.HCl [pH 8.0], 10 mM EDTA, 25 mM NaCl, 25% w/v Sucrose) supplemented with lysozyme (1.5 mg ml$^{-1}$). This treatment was carried out at 37° C. for 1 hr and the resulting sphereoplasts were lysed by the addition of 10% SDS (1.5% final conc.) To the cell lysate, solid caesium chloride was added at 1 g ml$^{-1}$. Once dissolved, ethidium bromide was added at 80 μg ml$^{-1}$ final conc. The suspension was then loaded into Sorvall Ultracrimp ultracentrifuge tubes and a gradient was established by centrifugation at 30,000 rpm at 20° C. for 72 hrs. Once resolved and visualised by an intense ethidium bromide band, the genomic DNA was removed by syringe. Ethidium bromide was removed by extraction with caesium chloride-saturated butanol. Finally, the genomic DNA was dialysed in 10,000 volumes of TE buffer (10 mM Tris.HCl, 1 mM EDTA [pH 8.0]) with two changes.

A genomic library was prepared by a time-course partial restriction digest with Sami3A I (Promega Corp.) restriction endonuclease. Horizontal agarose gel electrophoresis resolved DNA fragments in the range of 1.0–4.0 kb. These fragments were excised by electroelution in TBE (16mM Tris. HCl [pH 8.0], 8mM Boric acid, 400 μM EDTA) at 25 mA current. The eluted DNA fragments were purified by extraction with an equal volume of Tris-buffered phenol:chloroform and ethanol precipitation. The Sati3A I partial genomic DNA fragments were ligated into pUC19; see Yanish-Peron et al, Gene 33:103–119 (1985). The cloning vector pUC19 had been previously linearised by BamHI (Promega Corp.) restriction digestion and 5'-phosphate groups were removed by Calf Intestinal Alkaline Phosphatase (Promega Corp.) to prevent re-ligation. Ligations were carried out at 14° C. with various ratios of vector and genomic fragments using T4 DNA ligase (Boehringer Mannheim Ltd). Ligation reactions were transformed into Max Efficiency E. coli DH5α (Gibco BRL Life Sciences), transformed E. coli were plated onto Tryptone Soya Agar (Oxoid Ltd) supplemented with ampicillin (100 μg ml$^{-1}$), X-Gal (50 μg ml$^{-1}$), and 1 rnM IPTG. After overnight incubation at 37° C., transformed E. coli colonies were adsorbed onto Whatman 2 filter paper discs impregnated with 20mg ml$^{-1}$ (+)-lactam in methanol. Filters were incubated at room temperature for 4 hrs and developed with 2% w/v ninhydrin in acetone. After developing at 60° C., a distinctive brown halo upon a purple background, indicative of amino acid production, could be clearly seen around a single colony. The single lactamase-expressing clone was isolated and lactamase activity was verified by Achiral and Chiral HPLC assay.

7. Characterisation and Sequencing of Lactamase Gene

Plasmid DNA was prepared from the lactamase-expressing clone. Restriction digest analysis showed the presence of a 1.9 kb Sau3A I restriction fragment. DNA sequence analysis of the inserted fragment showed this fragment to incorporate a open reading frame (ORF) of 1.6 kb which, when driven by the upstream lac promoter of pUC19, translates to a protein of 575 residues (61 kDa.); see the Sequence Listing. The deduced amino acid sequence of the translated ORF shows >65% homology to the acetamidase from *Mycobacterium smegmatis* and *Methylophilus methylotrophus*. These enzymes have been shown to hydrolyse short chain fatty acylamides; see Draper, J. Gen. Microbiol. 46:111–123 (1969).

With reference to the Sequence Listing, the 1.9 kb lactamase fragment resides within the two preserved BamHI restriction sites. Sequence 5' to the insert incorporates the lac promoter and ribosome-binding site of pUC 19.

The pUC 19 construct carrying the lactamase gene was subsequently modified by the insertion of the cer element from the wild-type E. coli plasmid ColE 1. This construct was designated pPET1.

As will be understood, E. coli plasmid pPET1 was derived from pUC19, which harbours a 1.9 kb Sau3A I genomic fragment from *Comomonas acidovorans* ligated into the BamHI restriction site. The cer stability element of the wild type plasmid ColE 1 was inserted 3' to the lactamase fragment via BamHI (partial) and NdeI restriction.

8. Growth of Recombinant Lactamase

Recombinant E. coli strain was inoculated into a 1 litre baffled shake flask containing 100 ml TSB medium (Oxoid Ltd.) supplemented with ampicillin (100 gg ml$^{-1}$). The flask and inoculum were incubated for 16 hr at 37° C., shaking at 300 rpm in orbital shaker (25mm throw). The seed culture was inoculated (1%) into a 2.8 litre laboratory bioreactor vessel containing 1.5 litres TSB medium. The temperature was maintained at 25° C. pH 7.0, and dissolved O$_2$ tension at >50%. Growth was monitored at 520$_{nm}$, optical density against a TSB medium blank. After 24 hr growth, cells were harvested by centrifugation (5000 g at 4° C. for 10 min.). Cells were stored at −20° C. until required.

9. Use of Recombinant Cells

The E. coli strain harbouring the recombinant plasmid pPET1, was grown and stored as described above. Cells were resuspended at 10% w/v in 100 mM Tris.HCl, pH 7.5. Racemic lactam was resuspended of 100mg.mll in 100 mM Tris.HCl, pH 7.5. Reaction conditions for the biotransformation of (+)-lactam were 10mg ml$^{-1}$ of racemic lactam mixed with 0.1% w/v recombinant cells in 100 mM Tris.HCl, pH 7.5. The suspension was reacted at 25° C., shaking at 225 rpm for 1 hr. HPLC analysis after 1 hr reaction showed the conversion of 30% of (+)-lactam to acid with a selectivity of >95% ee.

What is claimed is:

1. An isolated enzyme capable of hydrolysing an enantiomer of the bicyclic lactam, 2-azabicyclo[2.2.1]hept-5-en-3-one, the enzyme having a stability characterised by hydrolysis at an initial concentration of 100 g racemic lactam plus 300 ml buffer and continuing to at least 90% hydrolysis of the (+) lactam with less than 5% hydrolysis of the (−) lactam.

2. The enzyme according to claim 1, having the characteristic that hydrolysis occurs at said initial concentration and continues to more than 98% of the (+) lactam with less than 2% hydrolysis of the (−) lactam.

3. An isolated ezyned capable of hydrolysing an enantiomer of the bicyclic lactam, 2azabicyclo[2.2.1]hept-5-en-one, obtaible from Comamonas acidovorans.

4. The enzyme according to claim 3, obtainable from Comamonas acidovorans, NCIMB 40827.

5. An isolated enzyme comprising the amino acid sequence shown in SEQ ID NO:2, or a fragment of SEQ ID NO:2 that is enzymatically active, capable of hydrolysing an enantiomer of the bicyclic lactam, 2-azabicyclo[2.2.1]hept-5-en-3-one and having a stability characterized by hydrolysis at an initial concentration of 100 g racemic lactam plus 300 ml buffer and continuing to at least 90% hydrolysis of the (+) lactam with less than 5% hydrolysis of the (−) lactam.

6. The enzyme according to claim 1, in immobilised form.

7. The enzyme according to claim 3, in immobilised form.

8. The enzyme according to claim 5, in immobilised form.

* * * * *

UNITED STATES PATENT AND TRADEMARK OFFICE
CERTIFICATE OF CORRECTION

PATENT NO. : 6,423,522 B1 Page 1 of 1
DATED : July 23, 2002
INVENTOR(S) : Richard Anthony Wisdom, Caroline Susan Lee and Robert Christopher Brown It is certified that error appears in the above-identified patent and that said Letters Patent is hereby corrected as shown below:

Column 16,
Line 63, "ezyned" should read -- enzyme --.
Lines 64-65, "2azabicyclo[2.2.1]hept-5-en-one, obtaible" should read
-- 2-azabicyclo[2.2.1]hept-5-en-3-one, obtainable --.

Signed and Sealed this

Twenty-ninth Day of October, 2002

Attest:

Attesting Officer

JAMES E. ROGAN
Director of the United States Patent and Trademark Office